US009282901B2

(12) United States Patent
Ostrow

(10) Patent No.: US 9,282,901 B2
(45) Date of Patent: *Mar. 15, 2016

(54) METHODS AND SYSTEMS TO CORRELATE ARRHYTHMIC AND ISCHEMIC EVENTS

(71) Applicant: Pacesetter, Inc., Sunnyvale, CA (US)

(72) Inventor: Eliot L Ostrow, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 308 days.

This patent is subject to a terminal disclaimer.

(21) Appl. No.: 13/855,574

(22) Filed: Apr. 2, 2013

(65) Prior Publication Data

US 2013/0218036 A1 Aug. 22, 2013

Related U.S. Application Data

(60) Division of application No. 12/770,598, filed on Apr. 29, 2010, now Pat. No. 8,433,397, which is a continuation of application No. 11/198,781, filed on Aug. 4, 2005, now Pat. No. 7,706,867.

(51) Int. Cl.
| | |
|---|---|
| A61B 5/04 | (2006.01) |
| A61B 5/02 | (2006.01) |
| A61B 5/0452 | (2006.01) |
| A61B 5/00 | (2006.01) |
| G06F 19/00 | (2011.01) |

(52) U.S. Cl.
CPC ........... *A61B 5/02007* (2013.01); *A61B 5/0452* (2013.01); *A61B 5/6846* (2013.01); *G06F 19/3487* (2013.01)

(58) Field of Classification Search
CPC ........................................................ A61B 5/04
See application file for complete search history.

(56) References Cited

U.S. PATENT DOCUMENTS 5,113,869 A * 5/1992 Nappholz et al. ............. 600/508

\* cited by examiner

*Primary Examiner* — Eric D. Bertram
*Assistant Examiner* — Elizabeth K So
(74) *Attorney, Agent, or Firm* — Theresa A. Raymer

(57) ABSTRACT

Systems and methods for determining whether there is a correlation between arrhythmias and myocardial ischemic episodes are provided. An implantable system (e.g., a monitor, pacemaker or ICD) is used to monitor for arrhythmias and to monitor for myocardial ischemic episodes. When such events are detected by the implantable system, the implantable system stores (e.g., in its memory) data indicative of the detected arrhythmias and data indicative of the detected myocardial ischemic episodes. Then, for each detected arrhythmia, a determination is made based on the data, whether there was a myocardial ischemic episode detected within a specified temporal proximity of (e.g., within a specified amount of time of) the arrhythmia. Where a myocardial ischemic episode occurred within the specified temporal proximity of an arrhythmia, data for the two events can be linked. Additionally, when a log of arrhythmias is displayed, for each arrhythmia there is an indication of whether a myocardial ischemic episode was detected within the specified temporal proximity of the arrhythmia. This abstract is not intended to be a complete description of, or limit the scope of, the invention.

20 Claims, 8 Drawing Sheets

```
┌─────────────────────────────────────────────────┐
│ display a log of detected myocardial ischemic   │── 602
│ episodes that indicates, for each ischemic      │
│ episode, whether there was an arrhythmia        │
│ detected within the specified temporal          │
│ proximity of the ischemic episode               │
└─────────────────────────────────────────────────┘
                        │
                        ▼
┌─────────────────────────────────────────────────┐
│ allow a user to select one of the ischemic      │── 604
│ episodes from the log                           │
└─────────────────────────────────────────────────┘
                        │
                        ▼
┌─────────────────────────────────────────────────┐
│ when an arrhythmia was detected within the      │── 606
│ specified temporal proximity to the selected    │
│ myocardial ischemic episode, display            │
│ information about the selected myocardial       │
│ ischemic episode and the arrhythmia             │
└─────────────────────────────────────────────────┘
```

US 9,282,901 B2

METHODS AND SYSTEMS TO CORRELATE ARRHYTHMIC AND ISCHEMIC EVENTS

PRIORITY CLAIM

This application is a Divisional application of and claims priority and other benefits from U.S. patent application Ser. No. 12/770,598, filed Apr. 29, 2010, entitled "METHODS AND SYSTEMS TO CORRELATE ARRHYTHMIC AND ISCHEMIC EVENTS", now U.S. Pat. No. 8,433,397, which is a Continuation of U.S. patent application Ser. No. 11/198,781, filed Aug. 4, 2005, entitled "METHODS AND SYSTEMS TO CORRELATE ARRHYTHMIC AND ISCHEMIC EVENTS", now U.S. Pat. No. 7,706,867. Each patent application identified above is incorporated herein by reference in its entirety to provide continuity of disclosure.

FIELD OF THE INVENTION

The present invention relates generally to implantable cardiac stimulation devices capable of myocardial ischemia and arrhythmia monitoring.

BACKGROUND OF THE INVENTION

Implantable cardiac stimulation devices are currently being used to treat various types of arrhythmias, such as ventricular tachycardia (VT) and ventricular fibrillation (VF). Such devices are capable of detecting the occurrence of an arrhythmia, and automatically applying an appropriate electrical stimulation or shock therapy to the heart aimed at terminating the detected arrhythmia. In addition to providing automatic stimulation, such devices often include a data acquisition system that is configured to acquire intracardiac electrogram (IEGM) signals, convert the raw analog data into digital signals, and store the digital signals for later processing and/or telemetric transmission to an external device.

Recently, there has been increased interest in adding myocardial ischemia detection capabilities to implantable cardiac devices. Myocardial ischemia, which involves oxygen starvation of the myocardium, can lead to myocardial infarction (MI) and/or the onset of malignant arrhythmias if the oxygen starvation is not alleviated. Although myocardial ischemia is sometimes associated with the symptom of angina pectoris (i.e., chest pain), many episodes of myocardial ischemia are asymptomatic or "silent." The inclusion of myocardial ischemia detection capabilities within an implantable device can provide a physician with information about a patient's ischemic burden, which is especially useful when the patient is suffering from silent ischemia.

While trending of ongoing ischemia burden is of interest, it has so far been unclear how to make such information actionable by a physician for things other than detection of risk of an acute myocardial infarction (MI). In other words, it is still generally unclear when a patient's chronic ischemic condition has grown bad enough to warrant pharmacologic therapy, or an angioplasty or coronary artery bypass procedure. Currently, it is likely that the physician will have to rely as much or more on patient symptomatology as on implantable device diagnostics to make such a determination. However, if it could be demonstrated that transient ischemic episodes were precipitating an increase in potentially lethal arrhythmias, a physician might deem such information as sufficient reason to intervene, regardless of the presence or absence of symptoms such as chest pain. Accordingly, there is a desire to provide physicians with information that will allow them to readily identify correlations between ischemic episodes and arrhythmias.

SUMMARY OF THE INVENTION

Embodiments of the present invention are related to systems and methods for determining whether there is a correlation between arrhythmias and myocardial ischemic episodes experienced by a patient. In accordance with embodiments of the present invention, an implantable system (e.g., a monitor, pacemaker or ICD) is used to monitor for arrhythmias and to monitor for myocardial ischemic episodes. When such events are detected by the implantable system, the implantable system stores (e.g., in its memory) data indicative of the detected arrhythmias and data indicative of the detected myocardial ischemic episodes. Then, for each detected arrhythmia, a determination is made based on the data, whether there was a myocardial ischemic episode detected within a specified temporal proximity of (e.g., within a specified amount of time of) the arrhythmia. In a specific example, there is a determination of whether there was one or more myocardial ischemic episode detected within the four hours leading up to an arrhythmia. This determination can be performed by the implantable system, but is preferably performed by a non-implanted system (e.g., a device programmer) that receives (e.g., uploads) the stored data from the implanted system.

In accordance with specific embodiments of the present invention, when a myocardial ischemic episode is detected within the specified temporal proximity of a detected arrhythmia, data indicative of the detected myocardial ischemic episode is linked with data indicative of the arrhythmia. This enables a user observing information about one type of event (e.g., an arrhythmia) to easily observe information about the other type of event (e.g., a myocardial ischemic episode), when these events occur within the specified temporal proximity to one another.

Certain embodiments of the present invention involve displaying a log of detected arrhythmias that indicates, for each arrhythmia, whether there was a myocardial ischemic episode detected within the specified temporal proximity of the arrhythmia. Preferably, a user observing the log can select one of the arrhythmias from the log. When a myocardial ischemic event was detected within the specified temporal proximity to the selected arrhythmia, information about the selected arrhythmia and information about the myocardial ischemic episode are both displayed. This will assist the user (e.g., a physician, clinician or technician) with determining whether one or more myocardial ischemic episode may have precipitated an arrhythmia.

Alternatively, or additionally, a log of detected myocardial ischemic episodes is displayed, wherein the log indicates, for each ischemic episode, whether there was an arrhythmia within the specified temporal proximity of the ischemic episode. Similarly, a user can select one of the myocardial ischemic episodes from the log, such that when an arrhythmia was detected within the specified temporal proximity to the selected myocardial ischemic episode, information about the selected myocardial ischemic episode and the arrhythmia are both displayed.

In accordance with other embodiments of the present invention, an implantable system is used to monitor for arrhythmias and to store, within the implantable system, data indicative of a detected arrhythmia and data indicative of a specified period leading up to the arrhythmia. Such data is then transmitted (periodically, or when the patient visits a physician's office) from the implantable system to a non-implanted system. For each arrhythmia, the non-implanted system can then determine based on the data indicative of the specified period leading up to the arrhythmia, whether there was a myocardial ischemic episode detected within the specified period leading up to the arrhythmia.

This summary is not intended to be a complete description of the invention. Other features and advantages of the invention will appear from the following description in which the preferred embodiments have been set forth in detail, in conjunction with the accompanying drawings and claims.

DETAILED DESCRIPTION OF PREFERRED EMBODIMENTS

The following description includes a best mode presently contemplated for the device. This description is not to be taken in a limiting sense but is made merely for the purpose of describing the general principles of the device. In the description that follows, like numerals or reference designators will be used to refer to like parts or elements throughout.

The disclosed systems and methods are directed to correlating arrhythmic and myocardial ischemic events. Thus, the methods described herein are intended for use with any implantable cardiac device capable of detecting arrhythmias and myocardial ischemic episodes. An exemplary implantable cardiac device will thus be described in conjunction with FIGS. 1 and 2, in which embodiments of the present invention described herein could be implemented. Additionally, FIG. 3 will be used to described an exemplary external programmer that can be used to program an implantable cardiac device, as well as upload information from implantable cardiac devices and analyze such information. It is recognized, however, that numerous variations of such a device exist in which the methods could be implemented.

Figure 1:
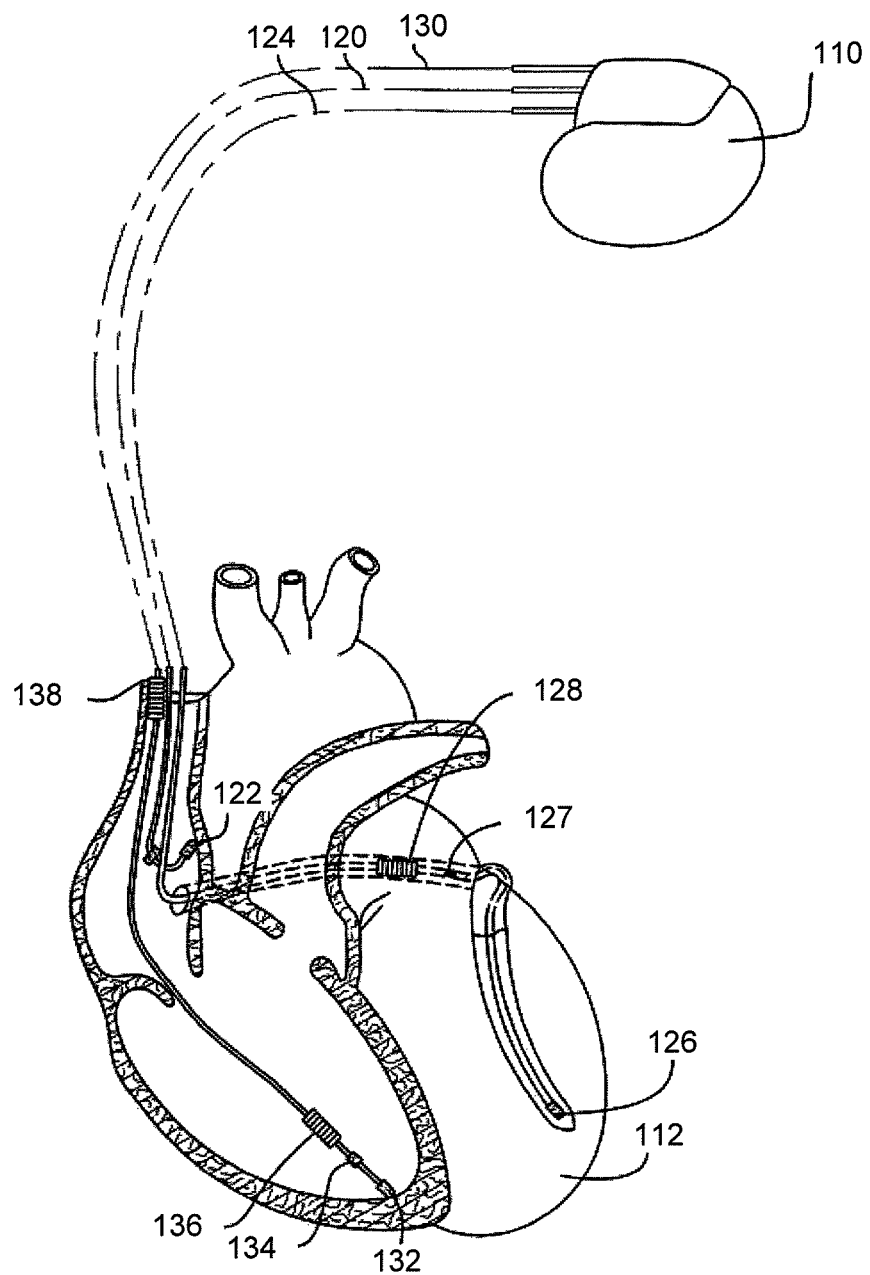
FIG. 1 is a simplified, partly cutaway view illustrating an implantable stimulation device in electrical communication with at least three leads implanted into a patient's heart for delivering multi-chamber stimulation and shock therapy.

Referring to FIG. 1, an exemplary implantable device 110 (also referred to as a pacing device, a pacing apparatus, a stimulation device, or simply a device) is in electrical communication with a patient's heart 112 by way of three leads, 120, 124 and 130, suitable for delivering multi-chamber stimulation. While not necessary to perform embodiments of the present invention, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention.

Figure 2:
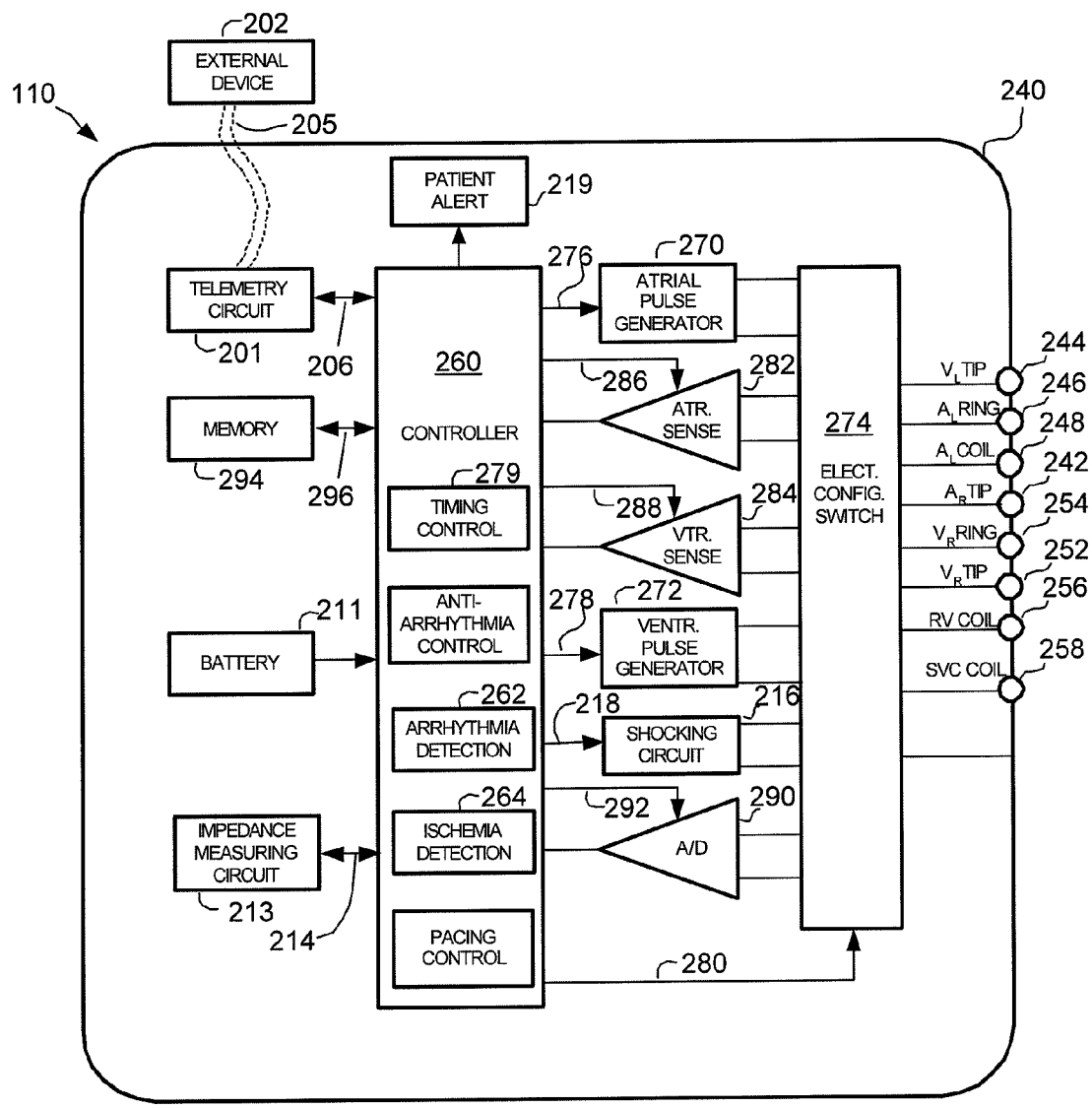
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 includes an arrhythmia detector 262 that utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 262 can be implemented within the microcontroller 260, as shown in FIG. 2. Thus, this detector 262 can be implemented by software, firmware, or combinations thereof. It is also possible that all, or portions, of the arrhythmia detector 262 can be implemented using hardware. Further, it is also possible that all, or portions, of the ischemia detector 262 can be implemented separate from the microcontroller 260.

Two exemplary types of arrhythmias that the arrhythmia detector 262 can detect include ventricular tachycardia (VT) and ventricular fibrillation (VF). A tachycardia is a fast heart rate (usually over 100 beats per minute) typically caused by disease or injury. It can also be part of a normal response to increased activity or oxygen demands. The average heart beats between 60 and 100 times per minute. When the tachycardia is due to disease or injury, it usually requires treatment. Tachycardias may begin in the upper chambers of the heart (the atria) or the lower chambers of the heart (the ventricles). A ventricular tachycardia (VT) begins in the ventricles. Some are harmless, but others are life threatening in that they can quickly deteriorate to a ventricular fibrillation.

A ventricular fibrillation (VF) is a very fast, chaotic heart rate (usually over 102 beats per minute) in the lower chambers of the heart, resulting from multiple areas of the ventricles attempting to control the heart's rhythm. VF can occur spontaneously (generally caused by heart disease) or when VT has persisted too long. When the ventricles fibrillate, they do not contract normally, so they cannot effectively pump blood. The instant VF begins, effective blood pumping stops. VF quickly becomes more erratic, resulting in sudden cardiac arrest. This arrhythmia must be corrected immediately via a shock from an external defibrillator or an implantable cardioverter defibrillator (ICD). The defibrillator stops the chaotic electrical activity and restores normal heart rhythm.

These are just two examples of the types of arrhythmias that the arrhythmia detector 262 can detect. One of ordinary skill in the art will appreciate that other types of arrhythmias can be detected, and information for such other types of arrhythmias can be stored. Examples of other types of arrhythmias that can be detected by the detector 262 include, but are not limited to, supraventricular arrhythmias (SVAs) and atrial arrhythmias such as atrial fibrillation (AF).

In accordance with embodiments of the present invention, the implantable device 110 can store, in memory 294, IEGM data corresponding to the period immediately prior to, during and subsequent to a detected arrhythmia. The implantable device can also store data that identifies the type of arrhythmia, the time of the arrhythmia (e.g., a time stamp), the duration of the arrhythmia, as well as any other type of information that a physician may deem useful. U.S. Pat. No. 4,295,474 (Fischell) and U.S. Pat. No. 5,732,708 (Nau et al.), each of which is incorporated herein by reference, provide exemplary additional details of the types of data that can be stored in response to the detection of an arrhythmia (and other cardiac events), and how such data can be efficiently and effectively stored. Using embodiments of the present invention, a physician can demonstrate when ischemic episodes may be precipitating an increase in potentially lethal arrhythmias, and thus, when to intervene (e.g., using pharmacologic therapy, an angioplasty or coronary artery bypass procedure), regardless of the presence or absence of symptoms such as chest pain.

In accordance with embodiments of the present invention, the implantable device 110 also includes an ischemia detector 264, which as described in more detail below, can detect ischemic events based, e.g., on ST-segment shift analysis. The ischemia detector 264 can be implemented within the microcontroller 260, as shown in FIG. 2. Thus, this detector 264 can be implemented by software, firmware, or combinations thereof. It is also possible that all, or portions, of the ischemia detector 264 can be implemented using hardware. Further, it is also possible that all, or portions, of the ischemia detector 264 can be implemented separate from the microcontroller 260.

The ischemia detector 264 can monitor sensed cardiac signals in order to detect and record timing and duration information relating to myocardial ischemic episodes. Ischemia detector 264 may also trigger a patient or physician alert in response to detecting a myocardial ischemic event. For example, a patient alert 219, which produces a vibratory or auditory alert, may be triggered.

There are many documented techniques for detecting episodes of myocardial ischemia. Many of these techniques perform ST-segment shift analysis to determine if there is a deviation of the ST-segment from a baseline (e.g., a PQ segment baseline), and detect myocardial ischemic events when the deviation is beyond a threshold. Other techniques are also possible. The precise technique used by the ischemia detector 264 to detect episodes of myocardial ischemia are not important to the present invention. Rather, what is important is that the ischemia detector 264 can detect episodes of myocardial ischemia and cause information relating to these episodes to be stored. For example, the implantable device 110 can store, in memory 294, IEGM data corresponding to the period immediately prior to, during and subsequent to a detected myocardial ischemic episode. The implantable device can also store data that identifies the ST-segment level during various portions of an episode (e.g., at onset of the ischemia, the peak of the ischemia and the termination of the ischemia), the time of the ischemic episodes (at onset, at peak and/or at termination), the duration of the episode, as well as any other type of information that a physician may deem useful. U.S. Pat. Nos. 6,112,116, 6,272,379 and 6,609,023 (all to Fischell et al.), which are incorporated herein by reference, provide exemplary additional details of the types of data that can be stored in response to the detection of a myocardial ischemic episode, and how such data can be efficiently and effectively stored.

Embodiments of the present invention, as will be described in more detail below, determine, or assist with the determination of, whether there is a correlation between arrhythmias and myocardial ischemic episodes experienced by a patient. Such information will enable a medical practitioner to analyze whether ischemic episodes that the patient experienced may have precipitated arrhythmias.

Still referring to FIG. 2, cardiac signals are also applied to the inputs of an analog-to-digital (ND) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes. In specific embodiments, the data acquisition system 290 may be used to acquire IEGM signals for the analysis of changes in the ST-segment for detecting myocardial ischemia.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy.

The operating parameters of the implantable device 110 may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the implantable device 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The above described implantable device 110 was described as an exemplary pacing device. One or ordinary skill in the art would understand that embodiments of the present invention can be used with alternative types of implantable devices. Accordingly, embodiments of the present invention should not be limited to use only with the above described device.

Figure 3:
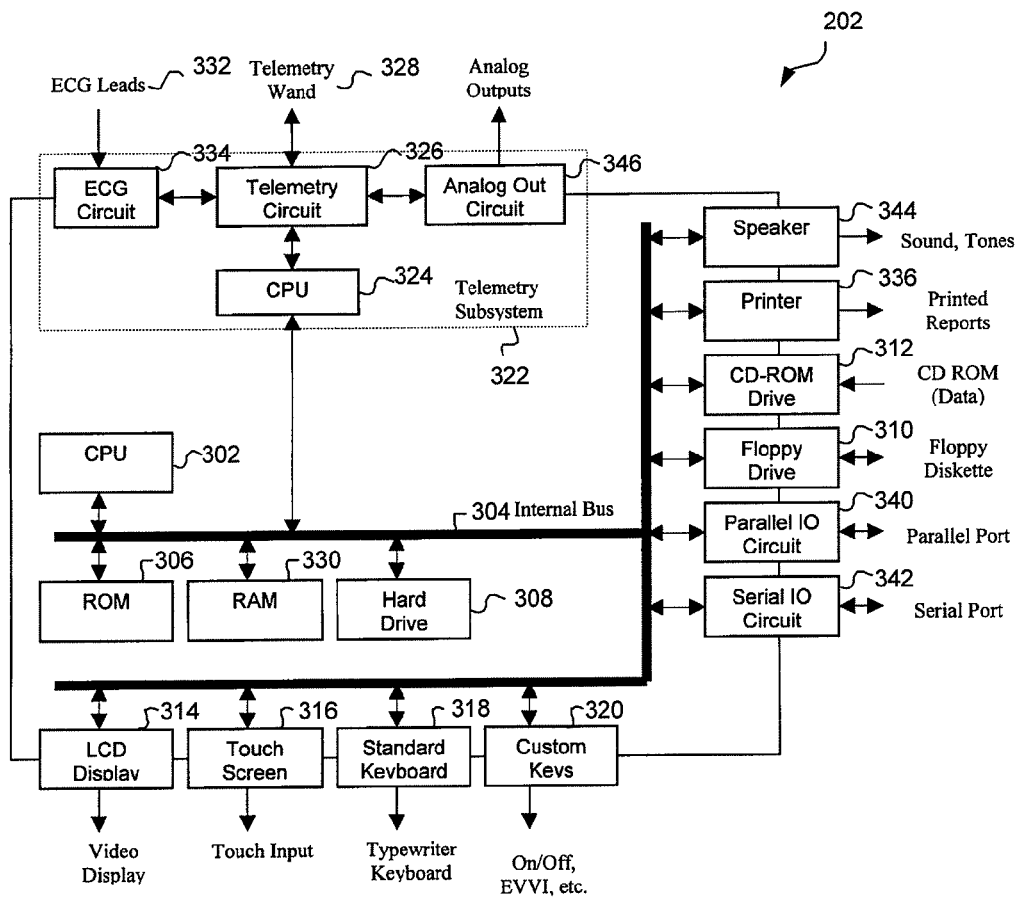
FIG. 3 is a functional block diagram of an exemplary external programmer device that can be used to program the implantable device of FIGS. 1 and 2, and to upload and analyze data collected by the implantable device.

FIG. 3 will now be used to illustrate components of an exemplary external programmer 202 for use in programming the implantable device 110, uploading data from the implantable device, and analyzing such data. Briefly, the programmer permits a physician or other user to program the operation of the implantable device 110 and to retrieve and display information received from the implantable device such as IEGM data and device diagnostic data. Additionally, the external programmer can receive and display EKG data from separate external EKG leads that may be attached to the patient. As will be described in further detail below, in accordance with embodiments of the present invention, the external programmer 202 is capable of processing and analyzing data received from the implantable device 110.

Operations of the programmer 202 are controlled by a CPU 302, which may be a generally programmable microprocessor or microcontroller or may be a dedicated processing device such as an application specific integrated circuit (ASIC) or the like. Software instructions to be performed by the CPU are accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU 302 displays a menu of programming options to the user via an LCD display 314 or other suitable computer display device. To this end, the CPU may, for example, display a menu of specific programming parameters of the implantable device to be programmed or may display a menu of types of diagnostic data to be retrieved and displayed. In response thereto, the physician enters various commands via either a touch screen 316 overlaid on the LCD display or through a standard keyboard 318 supplemented by additional custom keys 320, such as an emergency VVI (EVVI) key. The EVVI key sets the implantable device to a safe WI mode with high pacing outputs. This ensures life sustaining pacing operation in nearly all situations but by no means is it desirable to leave the implantable device in the EVVI mode at all times.

Once all pacing leads are mounted and the implantable device 110 is implanted, the various devices are programmed. Typically, the physician initially controls the programmer 202 to retrieve data stored within any implantable device 110 and to also retrieve EKG data from EKG leads 332, if any, coupled to the patient. To this end, the CPU 302 transmits appropriate signals to a telemetry subsystem 322, which provides components for directly interfacing with the implantable device 110, and the EKG leads. Telemetry subsystem 322 includes its own separate CPU 324 for coordinating the operations of the telemetry subsystem. Main CPU 302 of programmer communicates with telemetry subsystem CPU 324 via internal bus 304. Telemetry subsystem 322 additionally includes a telemetry circuit 326 connected to telemetry wand 328, which, in turn, receives and transmits signals electromagnetically from the telemetry unit 201 of the implantable device 110. The telemetry wand 328 is placed over the chest of the patient near the implantable device to permit reliable transmission of data between the telemetry wand 328 and the implantable device 110.

Typically, at the beginning of the programming session, the external programming device 202 controls the implantable device 110 via appropriate signals generated by the telemetry wand 328 to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implantable device such as lead impedances, battery voltages, battery recommended replacement time (RRT) information and the like. Data retrieved from the implantable device 110 is stored by external programmer 202 either within a random access memory (RAM) 330, hard drive 308 or within a floppy diskette placed within floppy drive 310. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implantable device 110 is transferred to programmer 202, the implantable device 110 may be further controlled to transmit additional data in real time as it is detected by the implantable device 110, such as additional IEGM data, lead impedance data, and the like. Additionally, or in the alternative, telemetry subsystem 322 receives EKG signals from EKG leads 332 via an EKG processing circuit 334. As with data retrieved from the implantable device itself, signals received from the EKG leads are stored within one or more of the storage devices of the external programmer. Typically, EKG leads output analog electrical signals representative of the EKG. Accordingly, EKG circuit 334 includes analog to digital conversion circuitry for converting the signals to digital data appropriate for further processing within programmer. Depending upon the implementation, the EKG circuit 334 may be configured to convert the analog signals into event record data for ease of processing along with the event record data retrieved from the implantable device. Typically, signals received from the EKG leads are received and processed in real time.

Thus, the programmer 202 can receive data both from the implantable device 110 and from the external EKG leads 332. As will be explained in more detail below, in specific embodiments of the present invention the programmer 202 receive arrhythmia data and myocardial ischemic episode data from the implantable device 110, thereby enabling the programmer 202 to analyze and display such data.

Data retrieved from the implantable device 110 includes parameters representative of the current programming state of the implantable device 110. Under the control of the physician, the external programmer 202 displays the current programming parameters and permits the physician to reprogram the parameters. To this end, the physician enters appropriate commands via any of the aforementioned input devices and, under control of CPU 302, the programming commands are converted to specific programming parameters for transmission to the implantable device 110 via telemetry wand 328 to thereby reprogram the implantable device 110. A wide variety of parameters may be programmed by the physician, including, but not limited to atrioventricular and inter-ventricular delay values. Prior to reprogramming specific parameters, the physician may control the external programmer 202 to display any or all of the data retrieved from the implantable device 110 or from the EKG leads, including displays of ECGs, IEGMs, and statistical patient information. Any or all of the information displayed by programmer may also be printed using a printer 336.

The programmer 202 also includes a modem 338 to permit direct transmission of data to other programmers via the public switched telephone network (PSTN) or other interconnection line, such as a T1 line or fiber optic cable. Depending upon the implementation, the modem may be connected directly to internal bus 304 may be connected to the internal bus via either a parallel port 340 or a serial port 342. Other peripheral devices may be connected to the external programmer via parallel port 340 or a serial port 342 as well. Although one of each is shown, a plurality of input output (IO) ports might be provided. A speaker 344 is included for providing audible tones to the user, such as a warning beep in the event improper input is provided by the physician. The telemetry subsystem 322 additionally includes an analog output circuit 346 for controlling the transmission of analog output signals, such as IEGM signals output to an EKG machine or chart recorder.

With the programmer 202 configured as shown, a physician or other user operating the external programmer is capable of retrieving, processing and displaying a wide range of information received from the EKG leads or from the implantable device 110 and to reprogram the implantable device 110 if needed. The descriptions provided herein with respect to FIG. 3 are intended merely to provide an overview of the operation of an exemplary external programmer 202 and are not intended to describe in detail every feature of the hardware and software of the device and is not intended to provide an exhaustive list of the functions performed by the device.

It is known that a patient that experiences frequent episodes of myocardial ischemia is at a high risk of experiencing a ventricular fibrillation (VF) or some other form of sudden cardiac death. In other words, the presence of myocardial ischemia correlates positively with a high risk for the development of VF or other forms of sudden cardiac death. However, what is not typically known is whether there is a causal relationship between myocardial ischemic episodes and VF for a specific patient, and more generally, whether there is a causal relationship between myocardial ischemic episodes and arrhythmias for a specific patient.

For example, if a device independently monitors for arrhythmias and myocardial ischemic episodes, and such information is displayed independently, it would be difficult to determine if there is a causal relationship between the two. More specifically, if during a period of time both the frequency of arrhythmias and the frequency of ischemic episodes increased, it would be difficult to say whether one caused the other, or whether a third factor caused both increases. One way for a physician to determine whether there is a causal relationship between the myocardial ischemic episodes and arrhythmias is for a physician to manually and laboriously study an arrhythmia log and a myocardial ischemia log in an attempt to see if such events coincide. However, such manual analysis may not be practical if such logs contain arrhythmia and ischemic episode data relating to numerous such events. Further, a physician is unlikely to recognize a correlation between ischemic and arrhythmic events unless the physician is specifically looking for such correlation. Thus, the physician may therefore overlook an important piece of clinical information, unless such information is brought to the physician's attention.

Embodiments of the present invention, as will be described below, provide practical ways for determining whether there may be a causal relationship between myocardial ischemic episodes and arrhythmias. More specifically, embodiments of the present invention will enable a physician to efficiently make determinations of whether myocardial ischemic episodes may be precipitating or contributing to the onset of arrhythmias.

Figure 4:
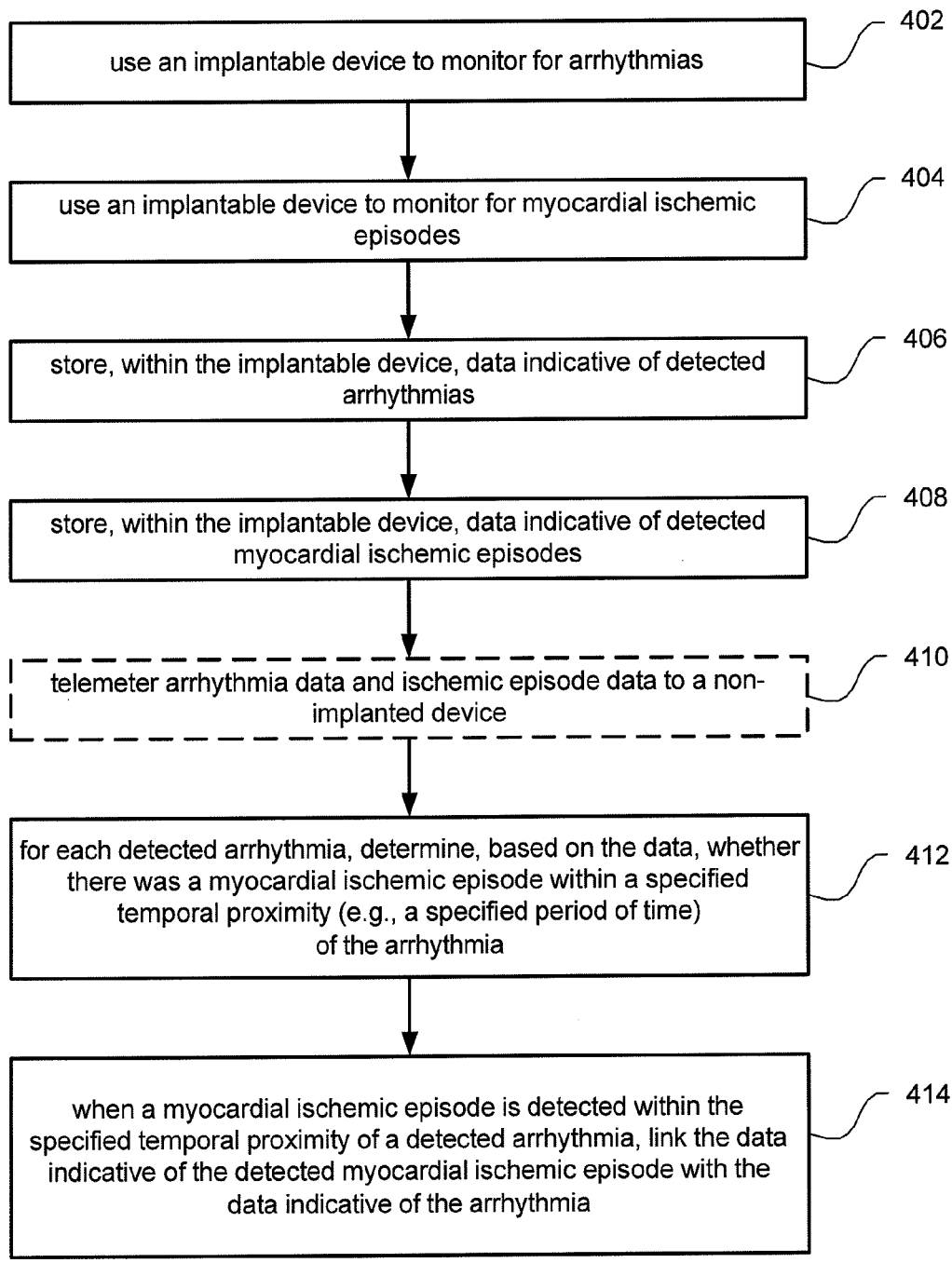
FIG. 4 is a high level flow diagram illustrating methods for determining correlations between arrhythmias and ischemic episodes, in accordance with embodiments of the present invention.

FIG. 4 is a high level flow diagram that is used to summarize specific embodiments of the present invention. In this flow diagram, and other flow diagrams presented herein, the various algorithmic steps are summarized in individual "blocks". Such blocks describe specific actions or decisions that must be made or carried out as the algorithm proceeds. Where a microcontroller (or equivalent) is employed, the flow diagrams presented herein provide the basis for a "control program" that may be used by such a microcontroller (or equivalent) to effectuate the desired control of the stimulation device. Those skilled in the art may readily write such a control program based on the flow diagrams and other descriptions presented herein.

Referring to FIG. 4, at step 402 an implantable system (e.g., a monitor, pacemaker or ICD) is used to monitor for arrhythmias, and as indicated at step 404 the implantable system is also used to monitor for myocardial ischemic episodes. For example, referring back to FIG. 2, the arrhythmia detector 262 of the implantable device 10 can be used to monitor for arrhythmias and the ischemia detector 264 can be used to monitor of myocardial ischemic episodes.

At steps 406 and 408, data indicative of detected arrhythmias and data indicative of detected myocardial ischemic episodes are stored within the implantable system. For example, referring back to FIG. 2, data indicative of detected arrhythmias and data indicative of detected myocardial ischemic episodes can be stored in the memory 294 of the implantable device 110. Examples of the type of information that may be stored for each detected arrhythmia include: IEGM data corresponding to the period immediately prior to, during and subsequent to a detected arrhythmia; the type of arrhythmia (e.g., VT or VF); the discriminators used to classify the arrhythmia; whether the discriminators agreed with one another; the rate of the arrhythmia; and time stamp data corresponding to the beginning and end of each arrhythmia. Examples of the type of information that may be stored for each detected myocardial ischemic episode include: IEGM data corresponding to the period immediately prior to, during and subsequent to a detected myocardial ischemic episode; data that identifies the ST-segment level during various portions of an episode (e.g., at onset of the ischemia, the peak of the ischemia and the termination of the ischemia); time stamp data corresponding to the onset, peak and termination of each ischemic episode; and the duration of the episode. These are just examples of the type of data that can be stored. One of ordinary skill in the art will appreciate from this discussion that additional and/or alternative types of data can also be stored.

At step 410, the arrhythmia and ischemic episode data is telemetered from the implantable device where the data was stored to an external device (e.g., device programmer 202) that can analyze the data. It is noted that this step is optional, and that some of the following steps can be performed within the implanted system. However, it is most efficient and logical for the following steps to be performed outside the implanted system, so as to minimize the processing and energy consumption of the implanted system.

At step 412, for each detected arrhythmia, there is a determination, based on the data, whether there was a myocardial ischemic episode detected within a specified temporal proximity of (e.g., within a predetermined amount of time of) the arrhythmia. The specified temporal proximity is preferably user programmable, such that a physician can define this threshold. An exemplary specified temporal proximity is "4 hours prior an arrhythmia." That is, in step 412, for each detected arrhythmia, there can be a determination of whether there was a myocardial ischemic episode detected during the four hour period leading up to the arrhythmia. This can be accomplished, for example, by comparing time stamps of detected arrhythmias to time stamps of detected myocardial ischemic events, and identifying those time stamps that are within the threshold of one another.

At step 414, when a myocardial ischemic episode is detected within the specified temporal proximity of a detected arrhythmia, data indicative of the detected myocardial ischemic episode is linked with the data indicative of the arrhythmia. This linking is preferably performed in such a manner that if further information about an arrhythmia is selected for display, further information about the myocardial ischemic episode that occurred within the specified temporal proximity of the arrhythmia is also displayed, and vice versa.

Figure 5:
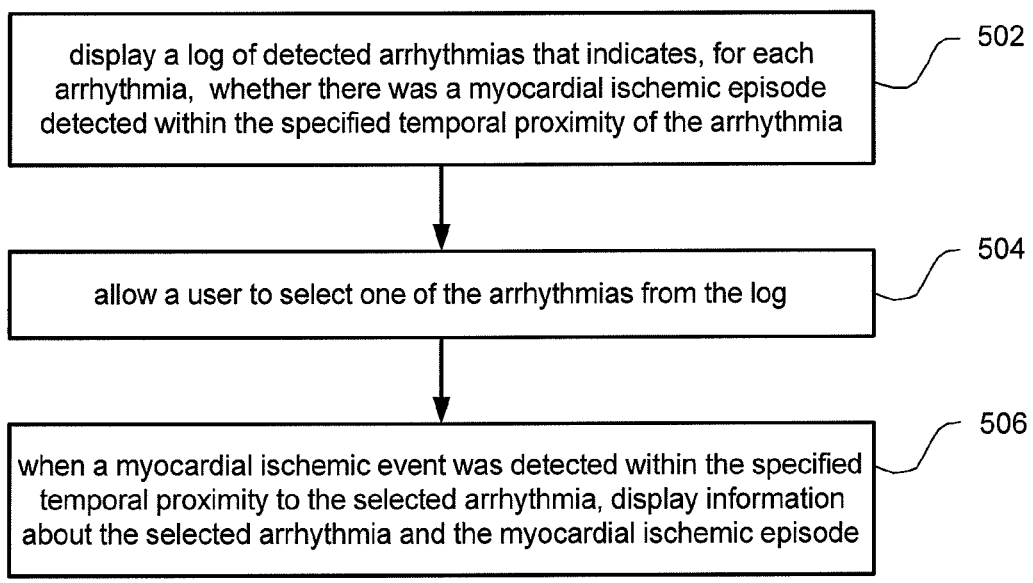
FIGS. 5 and 6 are high level flow diagrams that illustrates how information about arrhythmias and ischemic episodes can be displayed to a user in such a manner that a temporal relationship between the two are immediately apparent to the observer.

Embodiments of the present invention also include, as shown in FIG. 5 at step 502, displaying a log of detected arrhythmias that indicates, for each arrhythmia, whether there was a myocardial ischemic episode detected within the specified temporal proximity of (e.g., a predetermined amount of time of) the arrhythmia. Such a log can be displayed on the display 314 of the external programmer 202, or any other computer system that is used to display such information. It is also possible that such information may be displayed on a print out. The indicator, specifying that a myocardial ischemic episode was detected within the specified temporal proximity of the arrhythmia, can be accomplished in numerous ways. For example, the indicator can be a flag, asterisk, note or other similar indicator next to listed arrhythmic events, or such events can be highlighted, underlined, blinking, or the like.

At step 504, a user is allowed to select one of the arrhythmias from the log. For example, using a cursor, mouse, touch screen, or the like, a user is able to select or "click" on an entry in the log so that they can obtain additional information about a specific arrhythmic event.

As shown at step 506, when a myocardial ischemic event was detected within the specified temporal proximity of a selected arrhythmia, information about the selected arrhythmia and information about the myocardial ischemic episode are displayed for the user. Examples of the information about an arrhythmia that can be displayed include: IEGM plots corresponding to the period immediately prior to, during and subsequent to a detected arrhythmia; the name of the type of arrhythmia (e.g., VT or VF); information about the discriminators used to classify the arrhythmia; information about whether the discriminators agreed with one another; information about the rate of the arrhythmia; and timing information corresponding to the beginning and end of each arrhythmia. Examples of the type of information that may be displayed for a myocardial ischemic episode within the specified temporal proximity to the selected arrhythmia include: IEGM plots corresponding to the period immediately prior to, during and subsequent to a detected myocardial ischemic episode; information about the ST segment level during various portions of an episode (e.g., at onset of the ischemia, the peak of the ischemia and the termination of the ischemia); timing information corresponding to the onset, peak and termination of each ischemic episode; information about the amount of time between the ischemic episode (onset, peak and/or termination) and the arrhythmia; and information about the duration of the ischemic episode.

In accordance with the specific embodiments of the present invention, instead of displaying detailed arrhythmia information and ischemia information at the same time, whenever one type of information is displayed there can be a graphical link to the other type of information. This can be useful where the amount of information to be displayed for each type of event (i.e., the arrhythmic event and ischemic event) is sufficiently large that a display would be too busy or crowded if all the information were displayed at once.

These are just examples of the type of information that can be displayed. One of ordinary skill in the art will appreciate from this discussion that additional and/or alternative types of information can be displayed for arrhythmias and myocardial ischemic episodes.

If more than one myocardial ischemic episode occurred within the specified temporal proximity of the selected arrhythmia, all or some information about each ischemic episode can be displayed at the same time, or an indication of the plural episodes can be displayed to the user, and the user can be allowed to select from a list to obtain further information about specific episodes.

Figure 6:
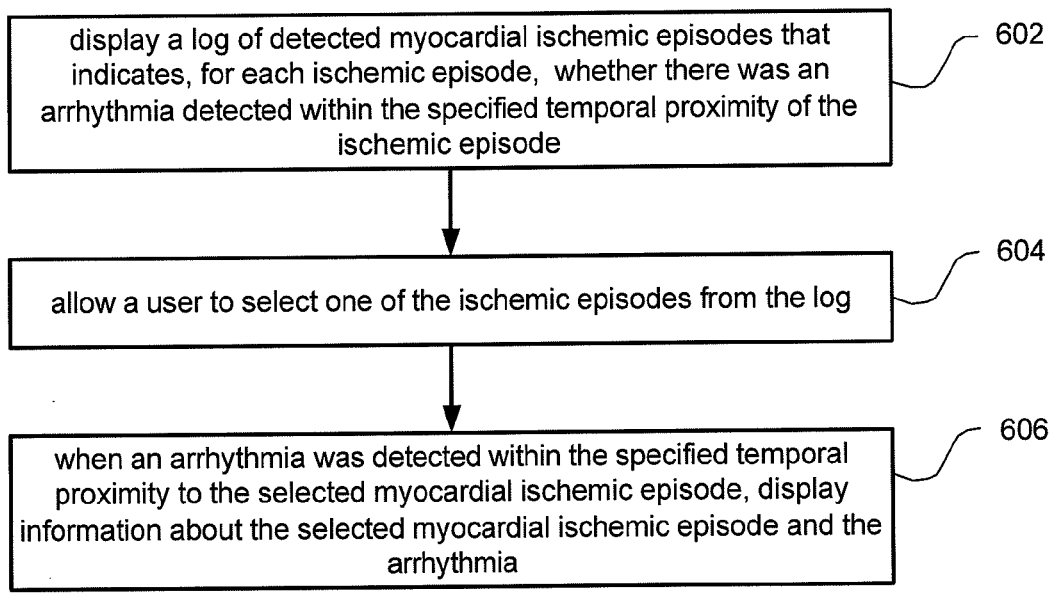

Referring now to step 602 of FIG. 6, in certain embodiments of the present invention, a log of detected ischemic episodes can be displayed such that there is an indication, for each ischemic episode, whether there was an arrhythmia detected within a specified temporal proximity of (e.g., four hours following) the ischemic episode. At step 604, a user is allowed to select one of the ischemic episodes from the log, in a similar manner as was discussed above with regards to step 504. At step 606, when an arrhythmia was detected within the specified temporal proximity to a selected ischemic event, information about the selected ischemic event and information about the arrhythmia can be displayed for the user, in a similar manner as was discussed above with reference to step 506.

The diagrams of FIGS. 5 and 6 explain how information about arrhythmias and ischemic episodes can be displayed to a user in such a manner that a temporal relationship between the two is immediately apparent to the user, without requiring that the user (e.g., physician, clinician, technician, etc.) manually and laboriously compare the information about each. These diagrams also explain how arrhythmia data and ischemic episode data can be linked in such a manner that information about one is easily obtained (e.g., displayed) when viewing information about the other.

Figure 7:
FIG. 7 illustrates an exemplary display log of detected arrhythmias that includes indications of whether there was a myocardial ischemic episode within a specified temporal proximity of each arrhythmia.

FIG. 7 illustrates an exemplary display log 702 of detected arrhythmias that can be displayed to a user. In this exemplary embodiment, there is an entire column 704 dedicated to indicating whether there was a myocardial ischemic event within a specified temporal proximity of each arrhythmia. However, as indicated above, other indicators, such as, but not limited to, highlighting, underlining, and asterisking, are within the scope of the present invention. From the log 702, a user can select a specific one of the arrhythmias to obtain additional information about the arrhythmia, as well as information about the myocardial ischemic episode (if one occurred within the specified proximal relationship of the selected arrhythmia). In one embodiment, a user can select (e.g., click on) the ischemic event indicator, and detailed information about that ischemic event can be immediately displayed.

Similarly, if a user was observing a myocardial ischemic episode log, there would be an indicator that specifies whether an arrhythmia occurred within the specified temporal proximity of each ischemic episode. A user can select a specific one of the episodes to obtain information about the ischemic episode, as well as information about the arrhythmia (if one was within the specific proximal relationship of the selected ischemic episode). In one embodiment, a user can select (e.g., click on) the arrhythmia indicator, and detailed information about that arrhythmia can be immediately displayed.

Figure 8:
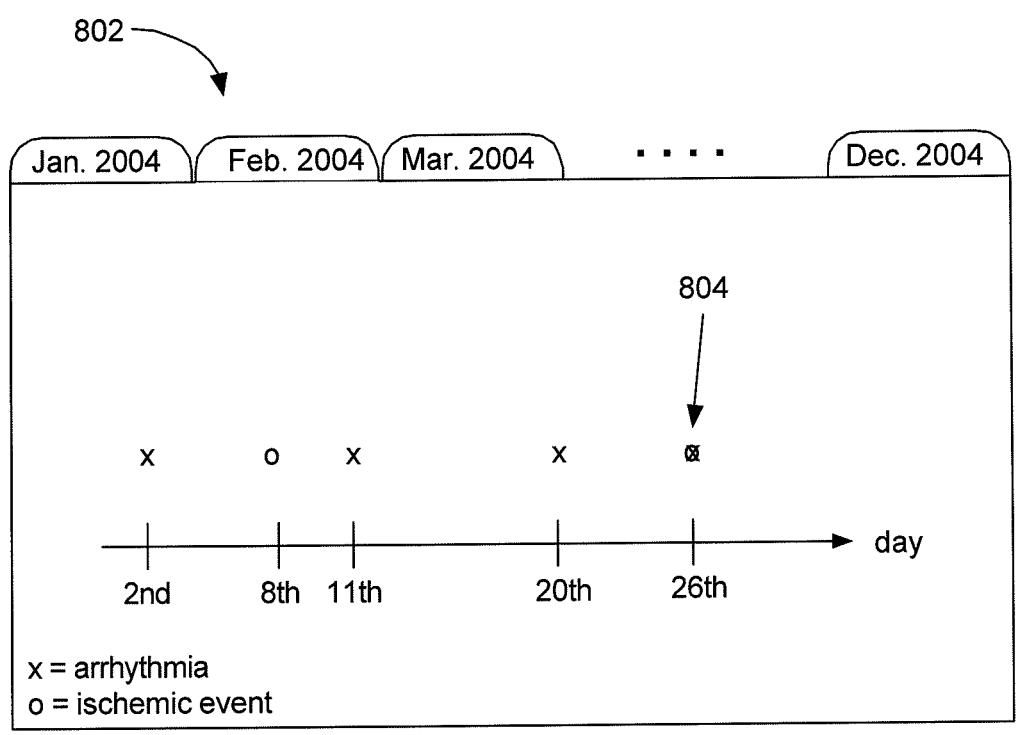
FIG. 8 illustrates an exemplary graph of detected arrhythmias and ischemic episodes that enables a person to see, at a glance, when a myocardial ischemic episode occurred within a specified temporal proximity of an arrhythmia.

FIG. 8 illustrates an exemplary graph 802 that enables a physician to see, at a glance, those periods of time (e.g., days) during which both an ischemic episode and an arrhythmia occurred. In the exemplary graph 802, an "x" indicates that an arrhythmia occurred on a specific day and an "o" illustrates that an ischemic event occurred on a specific day. If both an arrhythmia and an ischemic event occurred the same day, then the "x" and the "o" overlap or overlay one another, as shown at 804. In one embodiment, a user can select (e.g., click on) a day in the graph 802, and detailed information about event(s) that occurred on that day can be displayed. Where both an arrhythmia and an ischemic event occurred on the same day (or within some other specified temporal proximity), information about both events and their temporal proximity to one another can be displayed when that day is selected.

In accordance with a further embodiment, summary diagnostics can be presented to a physician. For example, a display may indicate how many arrhythmias out of a total number of arrhythmias during a specific period of time (e.g., a month) occurred within a specified temporal proximity of an ischemic episode. This can be presented, e.g., as N out of M arrhythmias occurred within the specified temporal proximity of an ischemic episode. Alternatively or additionally, this can be presented as a percentage of arrhythmias that occurred within the specified temporal proximity of an ischemic episode. One of ordinary skill in the art reading this description will realize that other manners of providing summary diagnostics are within the spirit and scope of the present invention. Such summary diagnostics can also be trended so a physician could see over a period of time (e.g., the life of an implantable device), whether there was a change in the correlation between ischemia and arrhythmia.

As mentioned above, the specified temporal proximity can be user programmable. In accordance with embodiments of the present invention, when a user changes the temporal proximity (i.e., specifies a new temporal proximity of interest), an updated arrhythmia and/or myocardial ischemic episode log, graph and/or summary diagnostic(s) can be produced and displayed to a user. For example, the specified temporal proximity can first be defined such that a myocardial ischemic episode is identified if it occurred within the four hours prior to an arrhythmia. A user may then change the temporal proximity to identify a myocardial ischemic episode that occurred within the six hours prior to an arrhythmia. Assuming there were some detected arrhythmias that did not have a myocardial ischemic episode in the four hours leading up to the arrhythmia, but did have a myocardial ischemic episode in the six hours leading up to the arrhythmia, then the log or graph (that includes indicators of whether there was a myocardial ischemic episode within the specified temporal proximity of the arrhythmia) and summary diagnostics (e.g., that indicates a percentage of arrhythmias that occurred within the specified temporal proximity) will change accordingly.

Alternative embodiments of the present invention can be use with an implantable system that does not include an ischemia detector 264. In such embodiments, an implantable system is used to monitor for arrhythmias and to store, within the implantable system, data indicative of a detected arrhythmia and data indicative of a specified period leading up to the arrhythmia. Such data is then transmitted (periodically, or when the patient visits a physician's office) from the implantable system to a non-implanted system. For each arrhythmia, the non-implanted system can then determine based on the data indicative of the specified period leading up to the arrhythmia, whether a myocardial ischemic episode occurred within the specified period leading up to the arrhythmia.

Embodiments of the present invention analyze and optionally display data in such a manner that it is immediately apparent when myocardial ischemic episodes and arrhythmias may be correlated. More specifically, embodiments of the present invention can be used to identify myocardial ischemic episodes that may precipitate an arrhythmia. Preferably, embodiments of the present invention present such information to a user in such a manner that the user need not manually and laboriously compare arrhythmia information with myocardial ischemia information. Embodiments of the present invention can also be used to link arrhythmia data and ischemic episode data in such a manner that information about one is easily obtained (e.g., displayed) when viewing information about the other.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 4-6. Further, it is possible to change the order of some of the steps shown in FIGS. 4-6, without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for determining whether there is a correlation between arrhythmias and myocardial ischemic episodes experienced by a patient, comprising:
   using an implantable system to monitor for arrhythmias and to monitor for myocardial ischemic episodes;
   storing, within the implantable system, data indicative of detected arrhythmias and data indicative of detected myocardial ischemic episodes;
   for at least one detected arrhythmia, determining using a microprocessor of an external programmer, based on the data, whether there was a myocardial ischemic episode detected within a specific programmed time duration of the arrhythmia; and
   displaying, on a display of the external programmer:
   a log or graph of detected arrhythmias that indicates, for each arrhythmia, whether there was a myocardial ischemic episode detected within the specific programmed time duration of the arrhythmia,
   a log or graph of detected myocardial ischemic episodes that indicates, for each myocardial ischemic episode, whether there was an arrhythmia detected within the specific programmed time duration of the myocardial ischemic episode, or
   summary diagnostics that indicates a percentage of arrhythmias that occurred within the specific programmed time duration of a myocardial ischemic episode.

2. The method of claim 1, further comprising:
   using the display to determine that there is a causal relationship between myocardial ischemic episodes and arrhythmias if there was a myocardial ischemic episode detected within a specific programmed time duration of the arrhythmia; and
   treating the patient's ischemic condition based on the causal relationship.

3. The method of claim 1, wherein the log of detected myocardial ischemic episodes includes an arrhythmia indicator, wherein the method further includes allowing a user to select the arrhythmia indicator, and wherein displaying, on a display of the external programmer comprises displaying information about an arrhythmia detected within the specified temporal proximity of the myocardial ischemic episode if the user selects the arrhythmia indicator.

4. The method of claim 1 wherein the specific programmed time duration is four hours.

5. The method of claim 1 wherein the specific programmed time duration is four to six hours.

6. A method for determining whether there is a correlation between arrhythmias and myocardial ischemic episodes experienced by a patient, comprising:
   obtaining, from an implantable system, data indicative of arrhythmias detected by the implantable system and data indicative of myocardial ischemic episodes detected by the implanted system;
   for each detected arrhythmia, using a microprocessor of an external medical device, automatically determining, based on the data, whether there was a myocardial ischemic episode detected within a specified temporal proximity of the arrhythmia; and if a myocardial ischemic episode is detected within the specified temporal proximity of the arrhythmia, using the microprocessor of the external medical device to link data indicative of the detected myocardial ischemic episode with data indicative of the arrhythmia and using a display of the external medical device to display at least one of:

the linked arrhythmia and ischemia data and their temporal proximity to one another, the arrhythmia data and a graphical link to the ischemia data, or the ischemia data and a graphical link to the arrhythmia data.

7. The method of claim 6, further comprising:
displaying with the display of the external medical device a log of detected arrhythmias that indicates, for each arrhythmia, whether there was a myocardial ischemic episode detected within the specified temporal proximity of the arrhythmia.

8. The method of claim 7, further comprising:
allowing a user to select one of the arrhythmias from the log; and
if a myocardial ischemic event was detected within the specified temporal proximity to the selected arrhythmia, displaying information about the selected arrhythmia and the myocardial ischemic episode.

9. The method of claim 6, further comprising:
displaying a log of detected myocardial ischemic episodes that indicates, for each episode, whether there was an arrhythmia within the specified temporal proximity of the episode.

10. The method of claim 9, further comprising:
allowing a user to select one of the myocardial ischemic episodes from the log; and
when an arrhythmia was detected within the specified temporal proximity to the selected myocardial ischemic episode, displaying information about the selected myocardial ischemic episode and the arrhythmia.

11. The method of claim 6, further comprising:
determining what percentage of detected arrhythmias during a period of time occurred within the specified temporal proximity of an ischemic episode; and
displaying the determined percentage.

12. The method of claim 6, further comprising:
determining what number of detected arrhythmias, out of a total number of detected arrhythmias during a period of time, occurred within the specified temporal proximity of an ischemic episode; and
displaying the determined number and the total number.

13. The method of claim 6, further comprising:
using the display to determine that there is a causal relationship between myocardial ischemic episodes and arrhythmias if there was a myocardial ischemic episode detected within specified temporal proximity of the arrhythmia; and
treating the patient's ischemic condition based on the causal relationship.

14. The method of claim 6 wherein the specified temporal proximity is four hours.

15. The method of claim 6 wherein the specified temporal proximity is approximately four hours.

16. A method for determining whether there is a correlation between arrhythmias and ischemic episodes experienced by a patient, comprising:
receiving from an implantable system, data indicative of detected arrhythmias and data indicative of a specified period leading up to each detected arrhythmia;
for each detected arrhythmia, determining, using a microprocessor of an external device, based on the data indicative of the specified period leading up to the arrhythmia, whether there was a myocardial ischemic episode that occurred within the specified period leading up to the arrhythmia;
displaying on an external display an indicator that there was a myocardial ischemic episode that occurred within the specified period leading up to the arrhythmia.

17. The method of claim 16, further comprising:
displaying a log of detected arrhythmias that indicates, for each arrhythmia, whether there was a myocardial ischemic episode that occurred within the specified period leading up to the arrhythmia;
allowing a user to select one of the arrhythmias from the log; and
when a myocardial ischemic event occurred within the specified period leading up to the selected arrhythmia, displaying information about the selected arrhythmia and the myocardial ischemic episode.

18. The method of claim 16, further comprising:
using the display to determine that there is a causal relationship between myocardial ischemic episodes and arrhythmias if there was a myocardial ischemic episode that occurred within the specified period leading up to the arrhythmia; and
treating the patient's ischemic condition based on the causal relationship.

19. The method of claim 16 wherein specified period is four hours.

20. The method of claim 16 wherein specified period is approximately four hours.

* * * * *

UNITED STATES PATENT AND TRADEMARK OFFICE
CERTIFICATE OF CORRECTION

PATENT NO. : 9,282,901 B2
APPLICATION NO. : 13/855574
DATED : March 15, 2016
INVENTOR(S) : Eliot L. Ostrow It is certified that error appears in the above-identified patent and that said Letters Patent is hereby corrected as shown below:

Title Page

At item (60), after "Division application No. 12/770,598, filed Apr. 29, 2010, now U.S. Pat. No. 8,433,397" please insert --, which is a continuation of application No. 11/198,781, filed Aug. 4, 2005, now U.S. Pat. No. 7,706,867--.

Signed and Sealed this
Fifth Day of July, 2016

Michelle K. Lee
*Director of the United States Patent and Trademark Office*